(12) United States Patent
Alessandri

(10) Patent No.: US 6,616,578 B2
(45) Date of Patent: Sep. 9, 2003

(54) COMPUTERIZED CONNECTION SYSTEM BETWEEN EXERCISE STATIONS FOR EXCHANGING COMMUNICATIONS OF RELATED USERS

(75) Inventor: Nerio Alessandri, Longiano (IT)

(73) Assignee: Technogym S.r.l., Gambettola (IT)

( * ) Notice: Subject to any disclaimer, the term of this patent is extended or adjusted under 35 U.S.C. 154(b) by 0 days.

(21) Appl. No.: 09/736,254

(22) Filed: Dec. 15, 2000

(65) Prior Publication Data

US 2001/0004622 A1 Jun. 21, 2001

(30) Foreign Application Priority Data

Dec. 21, 1999 (IT) ........................................ BO99A0700

(51) Int. Cl.$^7$ .............................................. A63B 22/00
(52) U.S. Cl. ................. 482/8; 482/4; 482/900
(58) Field of Search .................... 482/1–9, 900–902

(56) References Cited

U.S. PATENT DOCUMENTS

| | | | |
|---|---|---|---|
| 5,385,520 A | * 1/1995 | Lepine et al. .................. | 482/54 |
| 5,474,090 A | * 12/1995 | Begun et al. .................. | 482/1 |
| 5,645,509 A | * 7/1997 | Brewer et al. ................. | 482/4 |
| 5,842,958 A | 12/1998 | Rufa | |
| 5,890,995 A | 4/1999 | Bobick et al. | |
| 5,916,063 A | * 6/1999 | Alessandri ..................... | 482/4 |
| 5,984,839 A | 11/1999 | Corkum | |

FOREIGN PATENT DOCUMENTS

| | | |
|---|---|---|
| EP | 0919259 | 6/1999 |
| WO | WO 97/41925 | 11/1997 |

OTHER PUBLICATIONS

References mailed with application 09/690,701.*

* cited by examiner

*Primary Examiner*—Glenn E. Richman
(74) *Attorney, Agent, or Firm*—Arent Fox Kintner Plotkin & Kahn

(57) ABSTRACT

A computerized connection system between exercise stations, comprising an exercise machine or equipment item and interface means to allow the exchange of information between the user and the station itself, includes a telecommunication network operatively interposed between the exercise stations to allow the connection, information exchange and communication of the users of the individual stations.

26 Claims, 2 Drawing Sheets

COMPUTERIZED CONNECTION SYSTEM BETWEEN EXERCISE STATIONS FOR EXCHANGING COMMUNICATIONS OF RELATED USERS

BACKGROUND OF THE INVENTION

The present invention relates to the field of exercise machines and/or equipment and in particular its subject is a computerized communication systems for exchanging information and communications of the users of exercise stations.

The exercise stations of gyms for fitness or sports training can be constituted, as is generally known, by machines of by exercise equipment with various structures and features. Such stations can be equipped with electronic control and/or user interface means, constituted for instance by a system unit, by an input device, such as a keyboard, and by means for displaying the information, such as a monitor or display screen.

These electronic means allow the interaction between the user and the means embodying the actual exercise station for a broad variety of purposes, which can range from the simple recording of data pertaining to the user's work program; to the automatic pre-setting of the machine according to the various phases in the development of the user's program; to the feedback control of the machine and of the user to obtain an exact correspondence between the set program and the program actually performed.

Individual stations of the prior art, however, do not allow their respective users to communicate with each other, or vice versa to communicate with the world outside the space in which they are located.

Such a possibility would bring about significant advantages, since during the execution of the exercise the local users of a same gym, or the users of physically remote gyms could find it useful to be able to exchange information, messages, or even to participate in a collective, simultaneous exercise sections whilst being individually situated in physically remote locations.

SUMMARY OF THE INVENTION

The aim of the present invention therefore is to provide the users of two or more exercise stations, possibly also very remote from each other, with the capability of exchanging information in real time.

In accordance with the invention, said aim is achieved by a computerized telecommunication system for connecting the exercise stations, comprising an exercise machine or equipment item and user-to-machine interfacing means, characterized in that it further comprises a telecommunication network operatively interposed between the exercise stations and designed to connect individual users in such a way as to let them intercommunicate with each other or with the outside world.

BRIEF DESCRIPTION OF THE DRAWINGS

Further technical characteristics of the invention, according to the aforesaid aims, can be clearly noted from the content of the claims set out below and its advantages shall become more readily apparent in the detailed description that follows, made with reference to the accompanying drawings, which represent an embodiment provided purely by way of non limiting example, in which:

DESCRIPTION OF THE PREFERRED EMBODIMENTS

Figure 2:
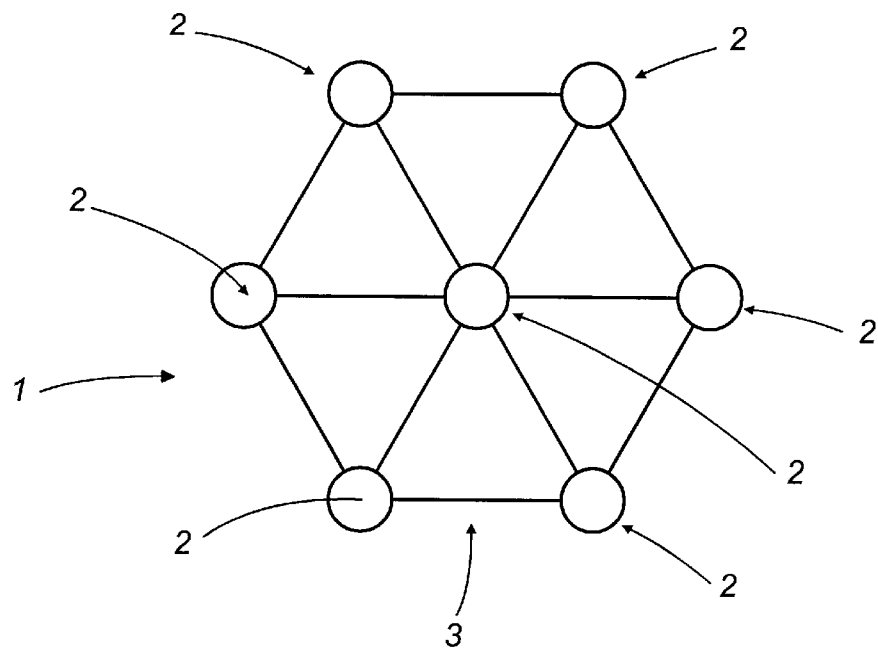
FIG. 2 is a schematic block representation of a system for the computerized connection of the exercise stations of FIG. 1.
Figure 3:
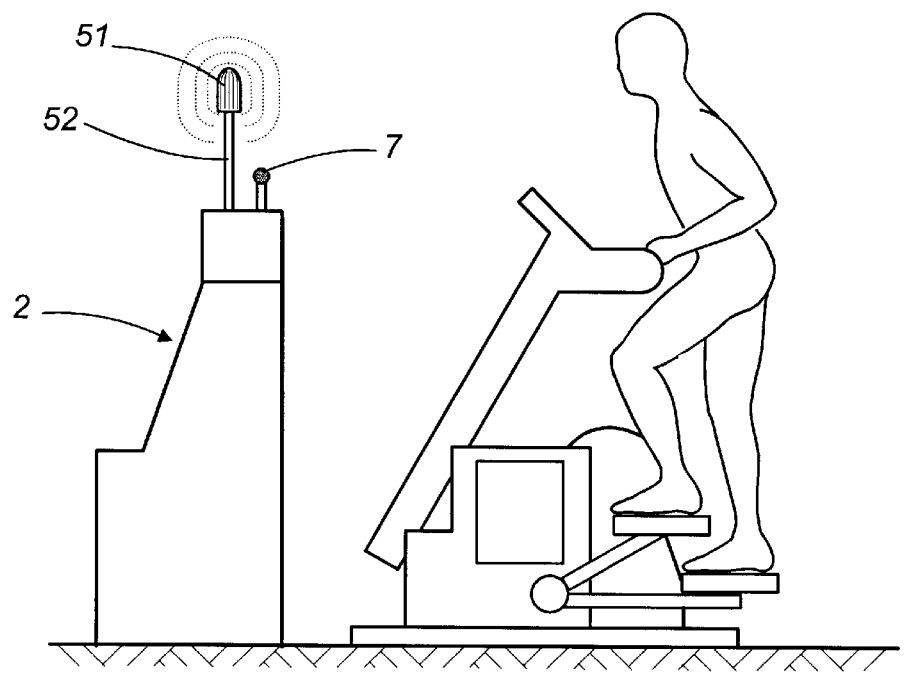
FIG. 3 is a schematic representation of an exercise station obtained according to the invention.

With reference to the drawing of FIG. 2, the number 1 globally indicates a computerized connection system between exercise stations 2 to allow the connection, and the exchange of information in general, between the users of individual stations 2, within the same gym, or vice versa, in a broader scope represented, for instance, by two distinct and separate physical environments, possibly situated in positions which can even be separated by a great distance.

The exercise stations 2 are operatively interconnected by an interposed telecommunication network 3.

The individual stations 2 are generally constituted by an exercise machine or equipment—which are not defined in detail because they are extraneous to the subject of the invention—comprising means for the interface between the user and the station 2 itself.

The interface means include a system unit 14 which allows, by means of a suitable software, the exchange of information between the user and the station 2 itself; or between the user and the organs 20 embodying the exercise machine, for setting up and controlling the machine itself; or also between the user and recording and controlling systems that record the progress of the personalized program, set up for the user.

The interface means between user and exercise station 2 generally comprise input means 4, 5, 6; 7; 8 and output means 9, 10; 11; 13 with which the user, through the network 3, activates a process of communication and bi-directional information exchange with the users of other exercise stations 2. Exchange, which through the adoption of suitable software and communication protocols can take place both in confidential form between only two users who are identified by means of appropriate recognition codes, or between a plurality of users who access a collective conversation through appropriate access filters.

In particular, the input means 4, 5, 6 can be made in such a way as to be able to be operated directly by the user of the exercise machine 2 itself and, as such, can be embodied by a keyboard 4—or by the same keyboard that normally equips the exercise station—or by a manually operated pointing device, such as a mouse 5 or joystick 6.

According to a different embodiment, particularly advantageous in the exercise stations 2 that provide for the user to employ his/her hands during the exercise, the input means can be so devised as to be operated by the user through voice activation. This can be obtained for instance by connecting, through a suitable audio board 21, a microphone 7 to the system unit 14.

The input means can also comprise at least a video camera 8 associated to the exercise station 2 and interfaced to the processing unit through suitable video board 25, whereby the users of the stations 2 simultaneously connected can also exchange visual data.

Figure 1:
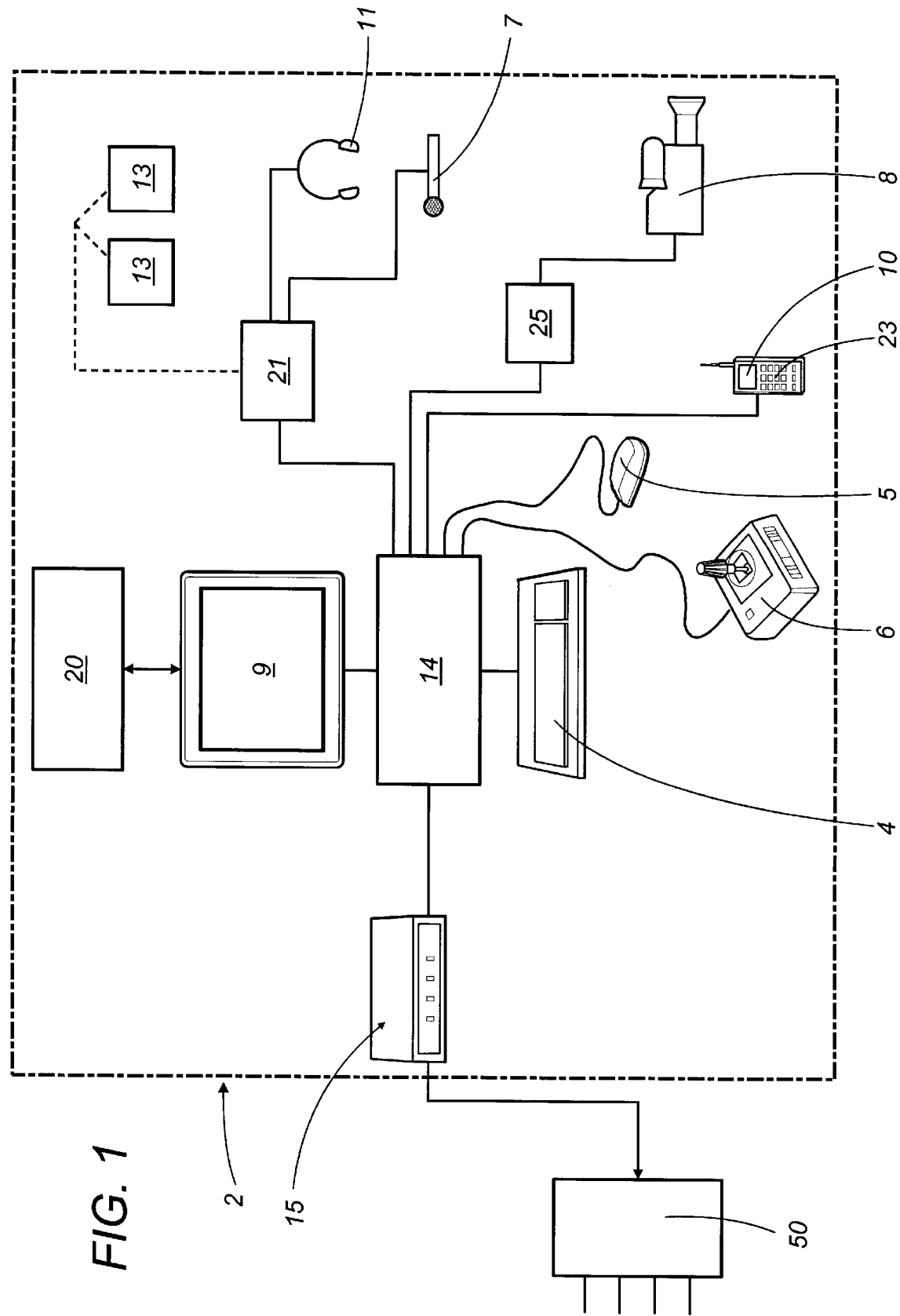
FIG. 1 is a heavily schematic block representation of an exercise station according to the invention.

In regard to the output means, FIG. 1 shows that they can comprise means for displaying the data embodied by a monitor 9 or by a display 10 provided to the exercise station 2; and they can further comprise, both in combination therewith and as an alternative thereto, an audio device 11

(i.e., ear phones) which can be worn by the user of the exercise station 2; or also one or more loudspeakers 13 associated to the exercise station 2 itself.

The telecommunication network 3 can be embodied by an analogue network; in this case the interface means between user and station 2 comprise a modem 15 for analogue-digital and digital-analogue conversion of the data exchanged between the users of the stations 2; but it can also be embodied by a digital data transmission network. The telecommunication network 3 can be physically supported by cables, by optical fibers, by wave guides; alternatively, it can be constructed also with a wireless technology and exploit, for instance, radio waves to transmit information between the users of the connected stations 2.

In use, the connection system of the invention allows all users who desire to exchange messages or to converse in real time during the execution of their respective exercises to communicate through the exercise stations 2.

However, further expansions and enhancements of such features are also possible, for it is readily understood that, through the local telecommunication network 3 of a generic gym, the user can reach the Internet global network and be able to communicate with other gyms, with individual exercise stations, which may be other users' home stations or, even more generally, with anyone with whom he/she desires to communicate during the execution of his/her own exercise program.

A possible indicative and non limiting example of such variations can be readily noted from FIG. 1, observing that the connection, through the network 3, of the various exercise stations 2 can also be activated through a simple portable telephone 23. The latter integrates within itself, by its construction, the keyboard and microphone as input devices, and the earphone device 11 and the display 10 as output devices.

The system according to the invention allows numerous and advantageous practical applications, a first example whereof is the possibility of favoring the socialization of the users of the exercise stations 2 of a gym. By providing each exercise station 2 with a microphone 7 and with a speaker 13 inter-operating with the telecommunication network 3, the users of the various exercise stations 2 can communicate with each other during the training session.

For this purpose the system is provided with search means 50 operating on the telecommunication network 3 to connect a first calling user with the exercise station 2 of a second called user, i.e. of a second user with whom the first desires to come in contact.

If the first, calling, user knows the physical location of the exercise station 2 of the called user, the search means can be embodied by a simple telephone router. If instead the first user desires to reach a second user without knowing the location of the second user's exercise station, the search means 50 will track the second user and, once identified his/her exercise station 2, will automatically connect him/her to the first, calling, user.

The recognition of the second user may take place both by means of dedicated hardware and by means of suitable software operating in such a way as to track the second user for instance by means of a suitable personal identification number entered in the exercise station 2, the so-called PIN, or through a portable means in which are stored various data both pertaining to the exercise protocol and to the personal recognition data; all as for instance illustrated in document IT-1.274.053, previously the subject of patent protection by the same Applicant.

Naturally, in order to preserve the privacy of the second user and his/her willingness to be contacted, the search means shall subordinate the connection of the second user to a declaration of availability for possible contacts which the second user may express by entering, from his/her own exercise station 2, an appropriate personal availability code; or also by activating or not activating an option presented for instance by a program menu.

The connection system described above can be advantageously employed also to allow an interactive dialogue between the instructor and the user of the exercise station 2, which in this case embody respectively the first and the second user as previously defined.

A further use of the system of the invention can be the formation of training classes, i.e. groups of users simultaneously engaged in a shared activity: in this case the first user, caller, connected to the telecommunication network 3 is again represented by the user; the second users, the called parties, shall instead be represented by the users of the various exercise stations 2 involved in the shared activity.

Naturally, it is also possible to obtain virtual training classes, in which the second users, the called parties, can be located in exercise stations 2 situated in mutually remote physical locations, such as gyms which may be in different cities, or also, more simply, inside rooms of individual homes.

In the case in which the training class is constituted by exercise stations 2 situated in the same room, the system can also comprise indicator means 51 able to signal that the user of a generic exercise station 2 is temporarily occupied in a connection with at least another user of the telecommunication network 3; or with a different operating move, that the user is available for socialization: the light signal can be seen as a complementary or alternative embodiment of the personal availability code.

More in particular, the indicator means can comprise a visual indicator 51, mounted on a support rod 52 associated to the exercise station 2. When the indicator 51 is used as a tool for identifying a training class, the emission of a light indication can allow immediately to highlight, in the plurality of the exercise stations 2 of the gym, which ones are simultaneously connected with the telecommunication network 3 and/or are collectively engaged in one of the possible activities which may be performed together.

By exploiting different chromatic tones of the light indicators, it shall be possible to distinguish the various training classes, which shall therefore be identifiable by instructors and users based on the tone set in the various exercise stations 2.

The invention is susceptible of evident industrial application and can be subject also to numerous embodiment variations without departing from the scope of the same inventive concept.

What is claimed:

1. A computerized connection system between exercise stations comprising:
   an exercise machine or equipment item;
   interface means to allow the exchange of information between a user and station, the interface means comprises means for the input and means for the output of information,
   a telecommunication network operatively interposed between the exercise stations to allow the connection and simultaneous bi-directional information exchange between the users of each individual station by allowing the socialization of the connected users.

2. A system as claimed in claim 1, wherein the input means is manually activated by the user of the exercise station.

3. A system as claimed in claim 2, wherein the input means is a keyboard or a pointing device which is manually activated by the user.

4. A system as claimed in claim 3, wherein the pointing device is a mouse or a joystick.

5. A system as claimed in claim 1, wherein the input means is vocally activated by the user.

6. A system as claimed in claim 5, wherein the input means a microphone.

7. A system as claimed in claim 1, wherein the input means comprises a video camera associated to the exercise station.

8. A system as claimed in claim 1, wherein the output means comprises means for displaying the information.

9. A system as claimed in claim 8, wherein the display means is a monitor or a display coupled to the exercise station.

10. A system as claimed in claim 8, wherein the output means comprises an ear phone device to be worn by the user of the exercise station.

11. A system as claimed in claim 1, wherein the output means comprises at least a loudspeaker associated to the exercise station.

12. A system as claimed in claim 1, wherein said telecommunication network is an analogue network, the interface means between user and exercise station comprises a modem for the analogue-digital and digital-analogue conversion of the information exchanged between the users of the exercise stations.

13. A system as claimed in claim 1, wherein said telecommunication network is a digital data transmission network.

14. A system as claimed in claim 1, wherein said telecommunication network transmits information in the form of radio waves.

15. A system as claimed in claim 1, wherein the system further comprises a microphone and a loudspeaker coupled to one exercise station and interoperating with the telecommunication network to help the socialization of the users connected to the telecommunication network.

16. A system as claimed in claim 15, wherein the system further comprises search means operating on the telecommunication network to connect a first, calling, user with the exercise station of a second, called, user, said search means connecting said users when the calling user knows the location of the exercise station of the called user.

17. A system as claimed in claim 15, wherein the system further comprises search means operating on the telecommunication network for automatically identifying the location of the exercise station of a second user to be called so that a first, calling, user is connected to the second, called, user.

18. A system as claimed in claim 16 or 17, wherein the search means subordinates the connection of said users to the availability of the second user, the availability being manifested by said second user by the emission of a personal availability code.

19. A system as claimed in claim 18, wherein the search means connects an instructor and at least a user of the exercise station.

20. A system as claimed in claim 19, wherein the search means connects a single calling user to a plurality of called users to form a class of called users participating in a shared activity.

21. A system as claimed in claim 20, wherein said called users are located in exercise stations situated in mutually remote physical locations.

22. A system as claimed in claim 21, wherein the system comprises indicator means for indicating that the user of an exercise station is temporarily occupied in a determined activity.

23. A system as claimed in claim 22, wherein the system comprises indicator means for indicating that the user of an exercise station is temporarily occupied in a connection with at least another user of the telecommunication network.

24. A system as claimed in claim 23, wherein said indicator means indicates, with a visual signal, that said user of the exercise station is temporarily occupied in a connection with the telecommunication network.

25. A system as claimed in claim 24, wherein said indicator means comprises a visual indicator mounted on a support rod associated to the exercise station.

26. A system as claimed in claim 25, wherein said indicator means identifies the users of the exercise stations occupied in a common connection by identically colored visual indications.

* * * * *